US00PP18212P2

(12) United States Plant Patent
Kaagman

(10) Patent No.: US PP18,212 P2
(45) Date of Patent: Nov. 13, 2007

(54) ***CAMPANULA* PLANT NAMED 'CAMP INBULE'**

(50) Latin Name: ***Campanula* hybrid**
Varietal Denomination: Camp Inbule

(75) Inventor: Pim Kaagman, 1619 PE Andijk (NL)

(73) Assignee: Goldsmith Seeds Europe B.V., Andijk (NL)

( * ) Notice: Subject to any disclaimer, the term of this patent is extended or adjusted under 35 U.S.C. 154(b) by 0 days.

(21) Appl. No.: 11/412,519

(22) Filed: Apr. 27, 2006

(51) Int. Cl.
*A01H 5/00* (2006.01)

(52) U.S. Cl. ..... Plt./263

(58) Field of Classification Search ..... Plt./263
See application file for complete search history.

(56) References Cited

PUBLICATIONS

GTITM UPOVROM Citation for 'Camp Inbule' as per QZ PBR 20050114; Jan. 24, 2005.*

* cited by examiner

*Primary Examiner*—Kent L. Bell
(74) *Attorney, Agent, or Firm*—Jondle & Associates, P.C.

(57) ABSTRACT

A new *campanula* plant particularly distinguished by wide open, intense blue, star-shaped flowers, an early and floriferous flowering response, medium-green foliage with thin, cordate leaves, medium vigorous growth, well-branching with relatively thin stems and a low, mounding plant habit, is disclosed.

1 Drawing Sheet

Genus and species: *Campanula* hybrid.
Variety denomination: 'Camp Inbule'.

BACKGROUND OF THE NEW PLANT

The present invention comprises a new and distinct cultivar of *campanula,* botanically known as *Campanula* hybrid, and hereinafter referred to by the cultivar name 'Camp Inbule'. The new cultivar originated from a hybridization made in February 2001 in Andijk, The Netherlands. The female parent was 'CP-13-2', a proprietary interspecific hybrid (unpatented) blue-flowered *campanula* plant, while the male parent was 'CW-122-1', a proprietary (unpatented) blue-flowered *Campanula isophylla* plant. The seeds produced by the hybridization were sown in August 2001, and the resulting seedlings were selected in January 2002. A single plant selection was chosen for further evaluation and for asexual propagation in 2002.

The new cultivar was created in 2001 in Andijk, The Netherlands and has been asexually reproduced repeatedly by vegetative cuttings and tissue culture in Andijk, The Netherlands over a four-year period. 'Camp Inbule' has also been trailed at Hillscheid, Germany. The present invention has been found to retain its distinctive characteristics through successive asexual propagations.

Plant Breeder's Rights for this cultivar were applied for in Canada on Mar. 21, 2006 and with the European Union on Jan. 24, 2005.

SUMMARY OF THE INVENTION

The following are the most outstanding and distinguishing characteristics of this new cultivar when grown under normal horticultural practices in Andijk, The Netherlands and Hillscheid, Germany.

1. Wide-open, intense blue, star-shaped flowers;
2. An early and floriferous flowering response;

3. Medium-green foliage with thin, cordate leaves;
4. Well-branching with relatively thin stems;
5. Moderately vigorous growth; and
6. A low and mounding plant habit.

DESCRIPTION OF PHOTOGRAPH

This new *campanula* plant is illustrated by the accompanying photograph which shows overall plant habit including blooms, buds, and foliage of the plant; the colors shown are as true as can be reasonably obtained by conventional photographic procedures. The photograph is of a 5-month-old plant grown in a greenhouse in Andijk, The Netherlands in May 2003.

DESCRIPTION OF THE NEW CULTIVAR

The following detailed description sets forth the distinctive characteristics of 'Camp Inbule'. The data which define these characteristics were collected from asexual reproductions carried out in Andijk, The Netherlands. The plant history was taken partly on 5-week old plants, still in a vegetative state and grown in Hillscheid, Germany in the spring of 2006. Rooted cuttings were planted in 10.5-cm pots and grown in a greenhouse. The plants were not pinched. Flower observations were made on 35-week-old plants in fall of 2005. Color readings were taken under natural light. Color references are primarily to The R.H.S. Colour Chart of The Royal Horticultural Society of London (RHS) (2001).

DETAILED BOTANICAL DESCRIPTION

Classification:
*Family.*—Campanulaceae.
*Botanical.*—*Campanula* hybrid.
*Common name.*—Bellflower.

Parentage:

*Female parent.*—'CP-13-2', a proprietary blue-flowered interspecific hybrid *campanula* plant (unpatented).

*Male parent.*—'CW-122-1', a proprietary blue-flowered *Campanula isophylla* plant (unpatented).

Growth:

*Form.*—Herbaceous perennial; for commercial purposes the variety can be cultivated as an annual.

*Habit.*—Many basal branches; pinching results in a more even plant habit.

*Height* (*measured from the top of the soil*).—10 cm.

*Width* (*horizontal plant diameter*).—19 cm.

*Propagation.*—Terminal tips for cutting.

*Time to produce a finished flowering plant.*—11 to 13 weeks for a 10 cm to 12 cm pot.

*Outdoor plant performance.*—As flowering pot plants.

*Time to initiate and develop roots.*—25 days.

*Root description.*—Fibrous, fine and cream-white.

Stems:

*Average number* (*per plant*).—10 to 13.

*Length.*—11 cm to 13 cm.

*Diameter* (*at midpoint*).—0.2 cm to 0.2 cm.

Internode length.—1.0 cm to 1.5 cm.

*Color.*—RHS 143C.

*Anthocyanin.*—None.

*Texture.*—Nearly glabrous, sparse, fine pubescence.

Leaves:

*Arrangement.*—Alternate, simple.

*Size.*—Length: 3.5 cm to 4.0 cm. Width: 3.5 cm to 4.0 cm.

*Shape.*—Cordate to ovate.

*Margin.*—Dentate, somewhat irregular.

*Apex.*—Broadly acute to obtuse.

*Base.*—Cordate to slightly ovate or deltoid.

*Color.*—Immature leaves: Upper surface: RHS 143B. Lower surface: RHS 138B. Mature leaves: General: Medium green. Upper surface: RHS 137D. Lower surface: RHS 138B.

*Texture.*—Very short hair at the margins and along the leaf veins of the lower surface.

*Venation.*—Between palmate and pinnate.

*Venation color.*—RHS 138C, lower surface.

*Petioles.*—Length: Variable, up to 5.0 cm. Width: 0.2 cm. Color: RHS 141D. Texture: Sparse hair.

Flower bud:

*Shape.*—Narrow and oval (elongated) with furrows.

*Size.*—Length: 1.7 cm. Diameter: 0.7 cm.

*Color at tight bud.*—RHS 91A to RHS 91B.

Inflorescence:

*Blooming habit.*—Continuous under long-day conditions.

*Inflorescence type.*—Terminal, bending and decumbent.

*Number of flowers per inflorescence.*—About 5 to 8 flowers and buds.

*Lastingness of individual blooms on the plant* (*at 18° C.*).—About 14 days.

*Fragrance.*—None.

*Length.*—3.5 cm to 5.0 cm.

*Diameter.*—3.5 cm to 5.0 cm.

*Peduncle.*—Length: 2.0 cm to 4.0 cm. Diameter: 0.2 cm. Color: RHS 143B. Texture: Nearly glabrous, sparse pubescence.

*Pedicels.*—Length: 1.0 cm to 2.0 cm. Diameter: 0.1 cm to 0.2 cm. Color: RHS 143B. Anthocyanin: None. Texture: Glabrous.

Flowers:

*Flower type.*—Single, actinomorphic; campanulate.

*Corolla.*—Shape: Shallow cup-shape; composed of 5 acute lobes that are mainly fused and open outward. Size: Diameter: 3.8 cm to 4.0 cm. Depth: 0.8 cm. Color: General: Blue. Upper surface: RHS 92A. Lower surface: RHS 91A.

*Petals.*—Size: Length: 1.4 cm. Width: 1.2 cm. Quantity: 5. Apex: Acute. Base: Fused. Margin: Entire. Texture: Glabrous.

*Calyx.*—Composed of 5 sepals fused at the base.

*Sepals.*—Number: 5. Color: Upper surface: RHS 141C. Lower surface: RHS 141D. Length: 1.0 cm. Width: 0.4 cm. Shape: Lanceolate to narrow ovate. Apex: Acute. Base: Fused. Margin: Entire. Texture: Covered with sparse pubescence.

Reproductive organs:

*Stamens.*—Quantity: 5; coherent at the bases, enclosing the upper part of the ovary. Filament: Color: RHS N155A (whitish). Length: 0.1 cm to 0.2 cm (practically no free filaments). Diameter: 0.1 cm below the anthers. Anther: Color: RHS 163B (ochre). Size: Length: 0.3 cm to 0.4 cm. Diameter: 0.1 cm. Pollen: Color: RHS 162B (yellowish). Amount: Moderate. Pistil: Quantity: 1. Length: 1.6 cm. Stigma: Color: RHS 157D. Shape: 3-lobed with brush-like-arranged hair below the stigma. Style: Color: RHS 91A (light-blue) or lighter. Length: 1.2 cm. Ovary: Type: Intermediate. Shape: Oval. Length: 0.4 cm. Diameter: 0.3 cm. Color: RHS 143B (green).

Fruit and seed set: None observed.

Disease and insect resistance: No special observations made.

COMPARISON WITH PARENTAL AND COMMERCIAL CULTIVARS

'Camp Inbule' differs from the female parent 'CP-13-2' (unpatented) in that 'Camp Inbule' has larger flowers and larger leaves than 'CP-13-2'. Additionally, 'Camp Inbule' has a more mounding plant habit than 'CP-13-2'.

'Camp Inbule' differs from the male parent 'CW-122-1' (unpatented) in that 'Camp Inbule' has smaller flowers and a more compact plant habit than 'CW-122-1'. Additionally, 'Camp Inbule' has an earlier flowering response than 'CW-122-1'.

'Camp Inbule' differs from all known *Campanula* commerical varieties in that 'Camp Inbule' has a more compact plant habit, an earlier flowering response and a more evenly rounded plant habit than all of the known *Campanula* commercial varieties.

I claim:

1. A new and distinct cultivar of *campanula* plant as shown and described herein.

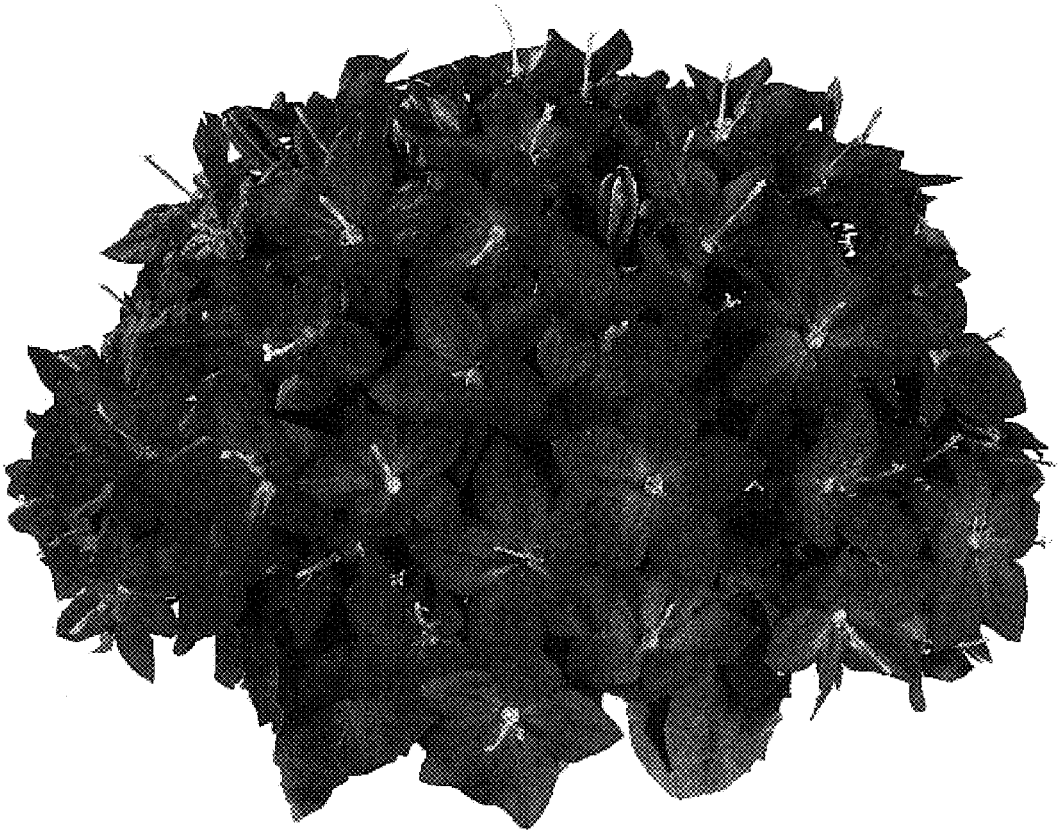

* * * * *